(12) United States Patent
Norberg

(10) Patent No.: US 7,696,176 B1
(45) Date of Patent: Apr. 13, 2010

(54) BLOOD REPLACEMENT PRODUCT

(76) Inventor: William J. Norberg, 2117 Sabinal St., Mission, TX (US) 78572

( * ) Notice: Subject to any disclaimer, the term of this patent is extended or adjusted under 35 U.S.C. 154(b) by 282 days.

(21) Appl. No.: 11/807,675

(22) Filed: May 31, 2007

(51) Int. Cl.
*A61K 38/00* (2006.01)
*A61K 35/16* (2006.01)
*C07K 14/00* (2006.01)

(52) U.S. Cl. ............................ 514/21; 514/2; 530/362; 530/363; 530/364; 530/830

(58) Field of Classification Search ........................ None
See application file for complete search history.

(56) References Cited

U.S. PATENT DOCUMENTS 6,867,193 B1 * 3/2005 Nakamura et al. ............ 514/21

* cited by examiner

*Primary Examiner*—Maryam Monshipouri
*Assistant Examiner*—Marsha M Tsay
(74) *Attorney, Agent, or Firm*—Frank A. Lukasik

(57) ABSTRACT

A composition comprising Human Serum Albumin and an Amino Acid Solution, a method of making the same, and a method for use, including treating acute hypovolemia due to any number of medical conditions due to sepsis with shock, hemorrhagic shock, hypovolemic shock, burn injury, capillary leak syndrome, hypoalbuminemia, nephritic syndrome, or multi-organ failure with third space fluid loss from any other medical disease.

2 Claims, No Drawings

BLOOD REPLACEMENT PRODUCT

FIELD OF THE INVENTION

The present invention relates generally to a blood replacement product, and more particularly to the combination of Human serum albumin and an amino acid solution.

BACKGROUND OF THE INVENTION

Human Serum Albumin is a Human blood derived product that is used to treat "Hypovolemia" as a blood replacer. Hypovolemia basically means low blood volume. "Hypo" means "low", "vol" is for volume, and "emia" refers to blood. Symptoms of hypovolemia may include cold hands and feet, lightheadedness, infrequent urination, increased heart rate, and weakness. Current estimate of use reports the current total volume of 450 metric tons of Human Serum Albumin is used world wide each year. Multiple products are under investigation as blood replacement products. Hetastarch, glycosolated hemoglobin. Polyethelene Glycol Modified Albumen, and Dextran compounds are some products that are currently used despite the limitations and complications associated with each product. Therefore, volume expansion or volume replacement with Human Serum Albumin continues to be a mainstay of current medical therapy.

A problem of displacement of albumin quite rapidly into the extracellular space limits the effectiveness and the benefit is therefore relatively short lived. This short half-life is a major problem especially if vascular integrity is compromised as the albumin leak may even exacerbate the extracellular space accumulation of water.

Extensive medical research about the effects of albumin is available. Likewise, extensive research is also available for basic amino acid solutions. Patterns and criteria for preparation and infusion of both components are well known.

Published U.S. Patent Application No. 200050187139 discloses a composition comprising an albumin-based coloid composition having at least one protected thiol region, method of making the same, and method for use, including treating hopovolemic conditions such as capillary leak syndrome and shock. One aspect of the application relates to a composition comprising an albumin-based colloid composition. In one aspect, the albumin-based colloid composition is modified such that its hydrodynamic radius is sufficiently large to preclude its leaking through the capillaries while retaining its oncotic properties and its ability to bind ligands such as sodium ions, fatty acids, drugs, and bilirubin.

U.S. Pat. No. 6,867,193 to Nakamura et al. discloses an albumin preparation containing amino acids.

SUMMARY OF THE INVENTION

The instant invention is a novel product created by the combination of Human Serum Albumin and an Amino Acid Solution. This new complex compound addresses the frequently encountered medical illness complications of hypovolemia and capillary leak syndrome. The instant invention is a blood replacement product. Although amino acids have been used and albumin has been used for years, there is no medical product available with the instant pattern of composition. Any usage has been related to the nutritional benefits of the amino acids. No other combinations have been used. The reason is that the human serum albumin is largely controlled by the blood banking programs and the amino acid component is controlled by the pharmacy industry. There are multiple commercial preparations of amino acid preparations and the most commonly used in the United States is TRAVASOL and these are readily available for purchase.

DETAILED DESCRIPTION OF THE INVENTION

The instant invention is a compound created by the mixture of albumin and an amino acid solution used for acute volume replacement manifested by hypovolemia and/or shock. This compound can be prepared with variable concentrations of human Albumin from 5% to 10% by weight combined with amino acid solution of 2% to 5%. Adjustment of the pH can be performed as needed for safe intravenous administration. Non-human sources of albumin may eventually be a satisfactory albumin product that performs the same physiologic benefit without the risks inherent in human blood products.

This combination of compounds can be adjusted to provide primarily oncotic pressure support with an increase in the albumin concentration or for homeostatic protein dynamics coupled with an increased concentration of amino acids to provide amino acids as nutritional for protein related healing and reparations.

The beneficial physiologic aspects of each component of the instant invention are maintained and desired medical benefits are enhanced by specific adjustments of the albumin and amino acid composition as the physiologic parameters of the disease state change with time.

The composite product of the invention consisting of human Serum Albumin and generally available amino acid solution is a new and previously unknown product. This new product has a varied molecular weight and molecular size much larger than either of the compounds individually. This new compound has weak bonding relationships that are physiologic in strength and therefor readily reversible. This large compound decreases the transudation of the simple albumin molecule through the capillary basement membrane pores resulting in the maintenance of an osmotic gradient to maintain volume within the vascular system.

Albumin is a small molecule with a hydrophilic component with its size increased by weak hydrophilic bonds to water molecules. The novel product of the invention described involves weak bonds that can be disjoined easily. The amino acid albumin compound has bonds to the amino acids that are stronger than the hydrophylic bonds to the water molecules but are still relatively weak forces. These bonds can be easily broken and the albumin used for gluconeogenesis and the amino acids can be incorporated into peptides for tissue reconstruction.

This is a method of addressing acute hypovolemia due to any number of medical conditions due to sepsis with shock, hemorrhagic shock, hypovolemic shock, burn injury, capillary leak syndrome, hypoalbuminemia, nephritic syndrome, or multi-organ failure with third space fluid loss from any other medical disease.

This compound provides and maintains physiologic balanced compounds that are available for energy sources via gluconeogenesis or for protein synthesis for healing.

Although the foregoing invention has been described in detail for purposes of clarity of understanding, it will be obvious that certain modifications may be practiced within the scope of the appended claims.

What is claimed is:

1. A composite product comprising 5% to 10% by weight of Human Serum Albumin and 2% to 5% by weight of Amino Acid Solution.

2. A method for treating acute hypovolemia due to a plurality of medical conditions selected from the group consisting of sepsis with shock, hemorrhagic shock, burn injury, capillary leak syndrome, hypoalbuminemia, nephritic syndrome, and multiorgan failure with third space fluid loss, said method consisting of injecting a composite product consisting of 5% to 10% by weight of Human Serum Albumin and 2% to 5% by weight of Amino Acid Solution to a patient in need thereof.

* * * * *